United States Patent
Francke et al.

(10) Patent No.: US 7,027,561 B2
(45) Date of Patent: Apr. 11, 2006

(54) DUAL-ENERGY SCANNING-BASED DETECTION OF IONIZING RADIATION

(75) Inventors: Tom Francke, Sollentuna (SE); Christer Ullberg, Sollentuna (SE)

(73) Assignee: XCounter AB, Danderyd (SE)

( * ) Notice: Subject to any disclaimer, the term of this patent is extended or adjusted under 35 U.S.C. 154(b) by 147 days.

(21) Appl. No.: 10/442,208

(22) Filed: May 21, 2003

(65) Prior Publication Data

US 2004/0234031 A1 Nov. 25, 2004

(30) Foreign Application Priority Data

Apr. 16, 2003 (SE) .................................. 0301132

(51) Int. Cl.
*G21K 5/10* (2006.01)
*G01N 23/06* (2006.01)

(52) U.S. Cl. .................. 378/146; 378/55; 378/156

(58) Field of Classification Search .................. 378/5, 378/54, 146, 157, 158, 55
See application file for complete search history.

(56) References Cited

U.S. PATENT DOCUMENTS

| 548,926 A | 10/1895 | Phelps |
| 4,020,347 A * | 4/1977 | Geluk ........................ 378/37 |
| 4,541,106 A | 9/1985 | Belanger et al. |
| 4,675,893 A | 6/1987 | Duinker et al. |
| 4,686,695 A * | 8/1987 | Macovski ................... 378/146 |
| 4,811,373 A * | 3/1989 | Stein ........................... 378/54 |
| 4,973,846 A | 11/1990 | Lanza et al. |
| 5,025,376 A | 6/1991 | Bova et al. |
| 5,040,199 A * | 8/1991 | Stein ........................... 378/56 |
| 5,164,977 A | 11/1992 | Vlasbloem et al. |
| 5,451,260 A | 9/1995 | Versteeg et al. ............. 118/725 |
| 5,570,403 A * | 10/1996 | Yamazaki et al. ............. 378/5 |
| 5,835,555 A * | 11/1998 | Barry et al. ................. 378/146 |
| 5,835,678 A | 11/1998 | Li et al. ..................... 392/401 |
| 5,882,416 A | 3/1999 | VanBuskirk et al. ........ 118/726 |
| 5,887,117 A | 3/1999 | Desu et al. ................. 392/386 |
| 6,067,342 A | 5/2000 | Gordon |
| 6,110,531 A | 8/2000 | Paz de Araujo et al. .......... 427/255.25 |
| 6,252,932 B1 | 6/2001 | Arakawa |
| 6,813,333 B1 * | 11/2004 | Karau et al. .................... 378/4 |

FOREIGN PATENT DOCUMENTS

| DE | EP 1192901 | 4/2002 |
| EP | 1 038 988 A2 | 9/2000 |
| JP | 11012741 A | 1/1999 |
| WO | WO98/31844 | 7/1998 |

* cited by examiner

*Primary Examiner*—Craig E. Church
*Assistant Examiner*—Thomas R. Artman
(74) *Attorney, Agent, or Firm*—Harness, Dickey & Pierce, P.L.C.

(57) ABSTRACT

A dual-energy scanning-based radiation detecting apparatus comprises a line detector; a device for scanning said line detector across an object while said line detector is exposed to an ionizing radiation beam, which has impinged on said object, to thereby record a plurality of line images of said object; a filter device arranged in the path of said ionizing radiation beam upstream of said object to filtrate said ionizing radiation beam, the filter device being capable of operating in two operation modes having different filter characteristics; and a control device for altering operation mode of the filter device subsequent to at least every second of said line images being recorded.

14 Claims, 8 Drawing Sheets

DUAL-ENERGY SCANNING-BASED DETECTION OF IONIZING RADIATION

FIELD OF THE INVENTION

The invention relates generally to apparatuses and methods for dual-energy scanning-based detection of radiation.

BACKGROUND OF THE INVENTION AND RELATED ART

Various line detectors for detecting ionizing radiation are known in the art. While such detectors provide for instantaneous one-dimensional imaging, two-dimensional imaging can only be performed by means of scanning the line detector, and optionally the radiation source, in a direction traverse to the one-dimensional detector array. Such scanning-based detection may be time consuming. Movement of the object being examined may occur during scanning, which would severely reduce the image quality obtained.

There are also known dual-energy detectors in the art, i.e. detectors, with which two images are produced using radiation of different energy and combined into a single image to enhance different elements in the image. Generally attenuation is a function of x-ray energy according to the two attenuation mechanisms photoelectric absorption and Compton scattering. These two mechanisms differ among materials of different atomic numbers. For this reason, measurements at two energies can be used to distinguish between different elements.

Dual-energy x-ray techniques can be used to identify bone tissue separately from soft tissue in medical imaging, for example, or to identify hazardous materials, for example, in baggage scanning.

SUMMARY OF THE INVENTION

However, when dual-energy imaging measurements are performed using a line detector, the object to be imaged has to be scanned twice—one time using radiation having a first radiation spectrum and then another time using radiation having a second radiation spectrum. To retrieve material-specific information the two images are compared at each position, i.e. on a pixel-based basis. The time lapsed between two detections at each position corresponds to the total scanning time for obtaining one two-dimensional image. This period of time may be large, e.g. several seconds, during which the object might have moved or have been moved. Particularly, when imaging living organisms, or portions thereof, it is expected that a considerable movement might have occurred on the time scale in question. Such movement renders the dual-energy comparison useless, or at least of significantly reduced quality.

Another option is to use two different radiation sources producing radiation of different energy. However, an additional radiation source adds to the cost for the equipment, and furthermore the sources have to be placed a certain distance from each other due to their size, and thus it is difficult to image the same point in the object simultaneously (or nearly simultaneously).

Still another option is to use a single radiation source, but alter its operation voltage between two different settings, at which radiation of different energy is produced. However, this adds a further time delay since the operation voltage of the radiation source cannot be altered instantaneously, and thus movement of the object may occur between the recordings of succeeding images.

A main object of the invention is therefore to provide a dual-energy scanning-based ionizing radiation detecting apparatus and method, which overcome or at least reduce the problem described above.

In this respect there is a particular object to provide such an apparatus and such a method, which are uncomplicated and can produce dual-energy high-quality two-dimensional images with excellent, signal-to-noise ratio, dynamic range, and image contrast.

A further object of the invention is to provide such an apparatus and such a method, which enable a fast scanning across the object to be examined.

A yet further object of the invention is to provide such an apparatus and such a method, which are reliable, accurate, and inexpensive.

These objects, among others, are attained by apparatuses and methods as claimed in the appended claims.

The inventors have found that by providing a filter device arranged in the path of a ionizing radiation beam upstream of an object, e.g. patient, to be examined in a dual-energy scanning-based measurement to filtrate the ionizing radiation beam, where the filter device is capable of operating in two or more operation modes having different filter characteristics, and wherein a control device alters operation mode of the filter device subsequent to at least every second of a number of line images being recorded by the scanning-based ionizing radiation detecting apparatus, a dual- (or multiple-) energy scanning-based imaging technique is obtained, where any movement of the examination object during scanning will affect the dual-energy images identically or at least similarly.

The inventors have also found that by using a scanning-based radiation detector apparatus comprising a plurality of stacked line detectors, each exposed to an ionizing radiation beam, a filter device may be arranged in the path of the radiation beams upstream of an object to be examined to filtrate the radiation beams, where the filter device comprises an array of filter sections aligned with the radiation beams so that each of the radiation beams will have been filtered by a respective one of the filter sections when impinging on the object, where every second filter section in the array has a first filter characteristic and each other filter section in the array has a second filter characteristic, and scanning may be performed with the array of filter sections kept aligned with the radiation beams across a distance corresponding to two times the distance between two adjacent line detectors of the stacked line detectors. Hereby, an high-quality dual-energy scanning-based imaging measurement is obtained, where corresponding pixels in the two images are recorded close in time to minimize problems in the dual-energy evaluation due to object movements.

The one-dimensional detector unit is preferably, but not exclusively, a gaseous based parallel plate detector unit. Other detector units that may be used include diode arrays, scintillator based arrays, CCD arrays, TFT- and CMOS-based detectors, liquid detectors, and solid-state detectors, e.g. one-dimensional PIN-diode arrays with edge-on, near edge-on or perpendicular incidence of X-rays.

Further characteristics of the invention, and advantages thereof, will be evident from the detailed description of preferred embodiments of the present invention given hereinafter and the accompanying FIGS. 1–9, which are given by way of illustration only, and thus are not limitative of the present invention.

DESCRIPTION OF PREFERRED EMBODIMENTS

Figure 1:
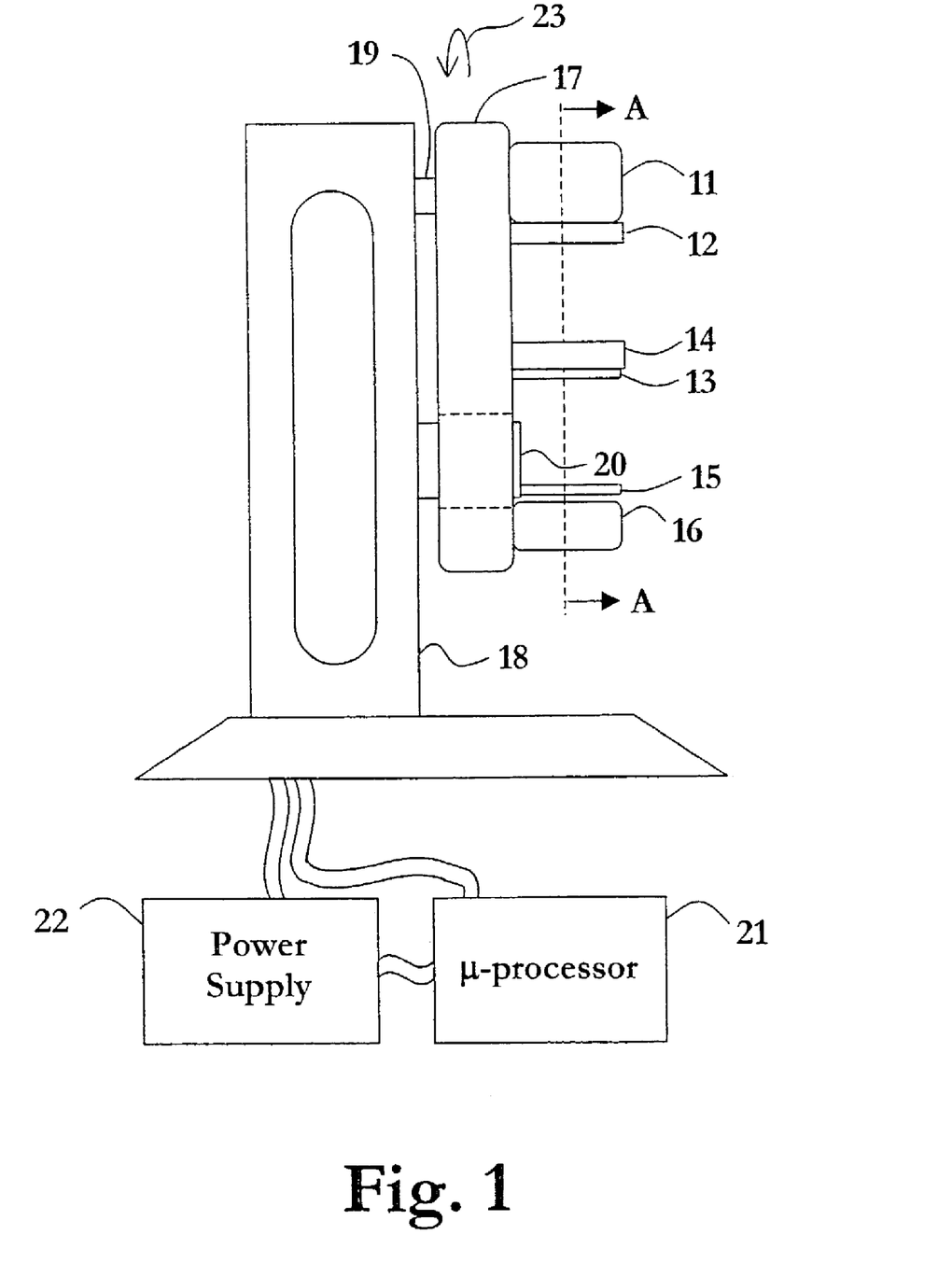
FIG. 1 illustrates schematically, in a side view, an apparatus for dual-energy scanning-based X-ray imaging according to a preferred embodiment of the present invention.

From top to bottom the apparatus in FIG. 1 comprises an X-ray source 11, a common filter 12, a dual- (or multiple-) energy filter device 14, a fan beam collimator 13, an object table or holder 15, and a one-dimensional detector unit 16.

The X-ray source 11 is a conventional X-ray tube having a cathode, which emits electrons, and an anode emitting X-rays in response to being struck by the electrons.

The common filter 12 is preferably located just beneath the X-ray tube 11, which typically includes thin metallic foils acting as filters to absorb the lowest (and sometimes also the highest) energy photons, which do not contribute significantly to the image quality. This filter is optional and can be part of the dual-energy filter device 14, described below.

The dual- (or multiple-) energy filter device 14 is preferably located just above the collimator 13. The filter device 14 has a variable spectral transmission characteristic to be discussed in detail further below.

The fan beam collimator 13, which is optional, may be a thin foil of e.g. tungsten with a narrow radiation transparent slit etched away. The slit is aligned with a corresponding line-shaped sensitive area or entrance slit of the detector unit 16 so that X-rays passing through the slit of the fan beam collimator 13 will reach the sensitive area of the detector unit 16.

Yet optionally, a further collimator is arranged in front of the detector (i.e. downstream of an object to be imaged).

Figure 2:
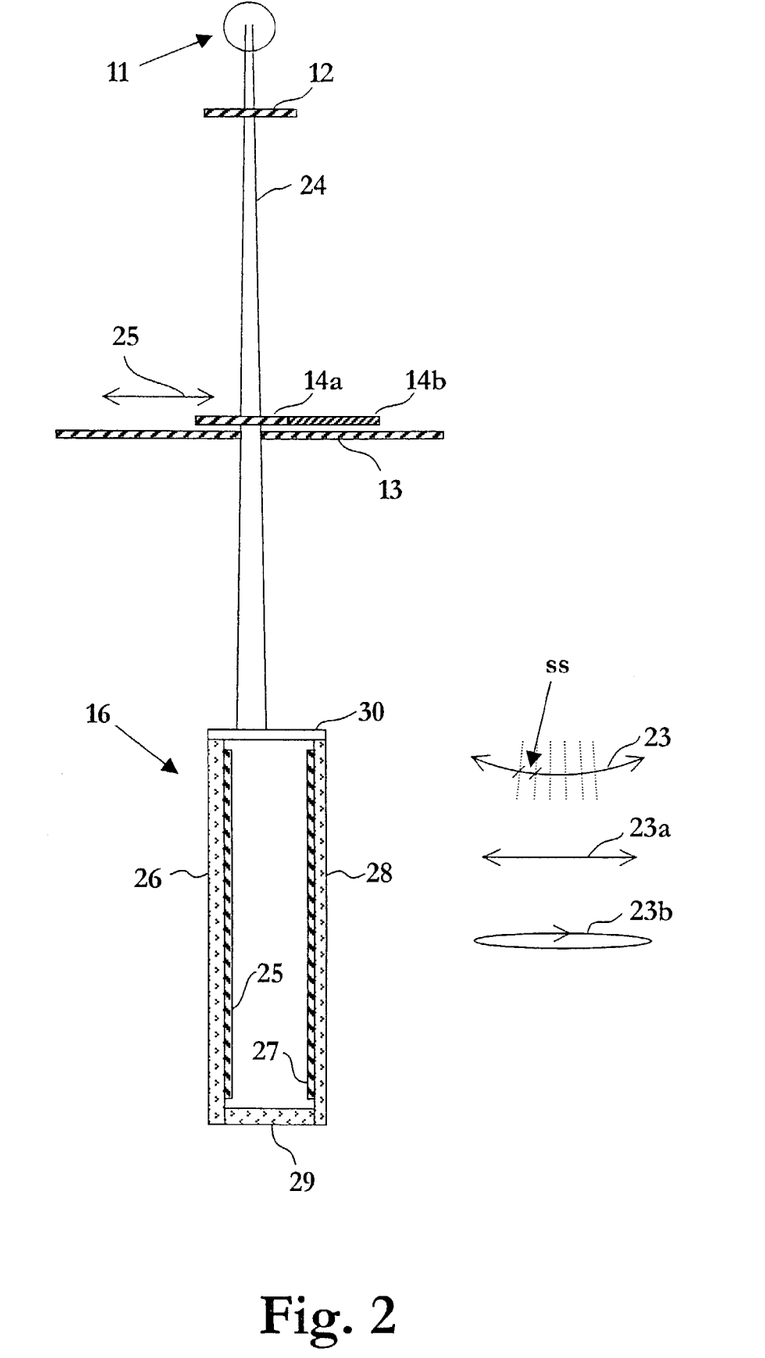
FIG. 2 is a schematic enlarged cross-sectional view of some of the components of the apparatus of FIG. 1 taken along the line A—A.

The detector unit 16 is illustrated more in detail in FIG. 2 and is oriented so that a planar or fan-shaped X-ray beam 24 can enter sideways between essentially planar cathode and anode arrangements. Each of the electrode arrangements includes an electrically conducting electrode layer 25, 27 supported by a respective dielectric substrate 26, 28, wherein the arrangements are oriented with the conductive cathode 25 and anode 27 layers facing each other. A radiation transparent window 30 is provided at the front of the detector unit to form an entrance for the fan-shaped beam 24 to the detector unit 16.

Preferably, the dielectric substrates 26, 28 and the window 30 define together with sidewalls 29 a gas-tight confinement capable of being filled with a gas or gas mixture, which is ionized by the incident radiation. Alternatively, the electrode arrangements are arranged within an external gas-tight casing (not illustrated).

A voltage is applied across the electrode arrangements to drift the electrons freed as a result of ionization towards the anode arrangement.

The detector unit 16 comprises further a readout arrangement including a one-dimensional array of individual readout elements for recording a one-dimensional image of the fan-shaped beam 24. Typically, the readout arrangement is integrated with the anode arrangement 27, 28. The detector unit 16 may also comprise capabilities for electron avalanche amplification in order to record very low flux of X-rays, or detect each single X-ray with high efficiency.

The X-ray tube 11, the common filter 12, the dual-energy filter device 14, the fan beam collimator 13 and the detector unit 16 are attached to a common E-arm 17, which in turn is rotatably attached to a vertical stand 18 by means of a spindle 19 approximately at the height of the X-ray tube 11. In this manner, the X-ray tube 11, the common filter 12, the filter device 14, the fan beam collimator 13 and the detector unit 16 can be moved in a common pivoting movement relative to an object to be examined arranged on the object table 15 to scan the object and produce a two-dimensional image thereof. The pivoting movement is schematically indicated by arrow 23. The object table 15 is firmly attached to a support 20, which in turn is firmly attached to the vertical stand 18. For this purpose the E-arm 17 is provided with a recess or similar in the E-arm 17 (illustrated by the dashed lines). During scanning, the object is kept still.

It shall be appreciated that the detector apparatus of FIG. 1 may be modified and arranged for linear movement of the X-ray tube 11, the common filter 12, the filter device 14, the fan beam collimator 13 and the detector unit 16 with respect to the object being examined. Such linear scanning movement is schematically indicated by arrow 23a in FIG. 2. Yet alternatively, the common filter 12, the filter device 14, the fan beam collimator 13 and the detector unit 16 may be rotated in the horizontal plane with respect to the object being examined as being schematically indicated by arrow 23b in FIG. 2. Such rotational-based scanning is disclosed in U.S. Pat. No. 6,067,342 (Gordon) and U.S. Pat. No. 5,025,376 (Bova et al.), the contents of which being hereby incorporated by reference.

It shall further be appreciated that the apparatus of FIG. 1 may be modified such that the object is moved during scanning, while the X-ray tube 11, the common filter 12, the filter device 14, the fan beam collimator 13 and the detector unit 16 are kept at rest.

Furthermore, the detector apparatus comprises a microprocessor or computer 21 provided with suitable software for controlling the apparatus and readout and post-processing of the signals from the line detector unit 16 and a power supply 22 for supplying the detector unit and the microprocessor or computer 21 with power and for driving a step motor or similar housed in the vertical stand 18 for driving the spindle 19 and thus the E-arm 17.

In operation, X-rays are emitted from the X-ray tube 11 and pass through the common filter 12, and the filter device 14. Only x-rays passing through the slit of the fan beam collimator 13 traverse the object. In the object, the X-ray photons can be transmitted, absorbed or scattered. The X-rays that are transmitted leave the object and enter into the detector unit 16 and are detected. From the detection a one-dimensional image of the object is formed.

It shall be appreciated by the person skilled in the art that instead of detecting X-rays that are transmitted, the detector apparatus may be arranged to detect X-rays that are scattered in some predetermined angle.

During scanning, the E-arm 17, holding the X-ray source 11, the common filter 12, the filter device 14, the fan beam collimator 13 and the detector unit 16, are moved in a pivoting movement such that the detector unit scans across the object in a direction, which is essentially parallel with the object table 15. At regular movement intervals, i.e. scanning distances ss, the detected signals are read out and stored in a memory of the microprocessor 21. When the scanning is stopped, a number of one-dimensional images of the object have been obtained, which are grouped together by the microprocessor 21 to create a two-dimensional image of the object. According to an alternative scanning technique the E-arm 17 is moved relative the object stepwise, and the one-dimensional detector unit 16 is detecting, while being still between the stepwise movements.

According to the present invention a dual-energy scanning is performed, which generally requires a specifically adapted filter device. To this end the filter device 14 is capable of operating in two operation modes having different filter characteristics.

One filter transmits preferably a low energy X-ray spectrum with average energy of typically 40 keV. This filter may be made of one or several thin foils of different elements. The filter elements are chosen such that the high-energy part of the incoming X-ray spectrum is absorbed in the filter. This can be achieved by using filter elements that have highly absorbing K-shell energies above the desired transmitted X-ray spectrum, e.g. cesium, barium, some of the lanthanides and/or heavier elements such as tungsten, gold or lead (with atomic number typically higher than 54).

The other filter transmits preferably a high-energy spectrum with average energy of typically 70 keV or higher. This filter may be made of one or several thin foils of different elements. The filter elements are chosen such that the low energy part of the incoming X-ray spectrum is absorbed in the filter. This can be achieved by using filter elements that have highly absorbing K-shell energies below the desired transmitted X-ray spectrum, e.g. cupper, molybdenum, silver etc. (with atomic number typically less than 64).

A control device is provided for altering operation mode of the filter device 14 subsequent to at least every second of the line images being recorded, e.g. every second line image is recorded using filtered radiation having a first radiation spectrum and the other line images are recorded using filtered radiation having a second radiation spectrum, or a repeated series of two line images being recorded using filtered radiation having the first radiation spectrum followed by two line images being recorded using filtered radiation having the second radiation spectrum is performed.

Typically, the filter device 14 is provided with two filter sections 14a, 14b as shown in FIG. 2, which sections have separate filter functions and which are capable of being arranged—one at a time—in the path of the radiation beam 24. A moving mechanism, e.g. housed in the E-arm 17, may be implemented to move the filter device 14 in directions of the bi-directional arrow 25 under control of the computer 21 to alternately arrange the two filter sections in the path of the radiation beam. Note that this movement will be superimposed on the scanning movement.

If the scanning is performed with a continuous scanning movement, preferably every second line image is recorded using filtered radiation having a first radiation spectrum and every second line image is recorded using filtered radiation having a second radiation spectrum. Provided that the scanning step is short, the misalignment, i.e. the pixel-to-pixel correspondence, in the dual-energy image evaluation is small, and provided that the detection time is short, movement of the object between the completion of the recordings of two subsequent line images is not occurring to any appreciable extent.

For instance, provided a scanning step of 50 microns and a line image exposure time of 1 ms, the misalignment in the pixel-to-pixel comparison will be about 50 microns (i.e. the two two-dimensional images are displaced on average 50 microns relative each other, whereas the two-line detection time will be 2 ms (if the time of detector electronics readout is negligible or may be performed in the background), during which time most macroscopic movements of living organisms may be considered to be "freezed". Such movements may include movements of hearts due to heartbeats, movements of chests due to inhalation and expiration, and movements of legs, arms, backs, and hips of patients.

However, the time needed for the recording of two complete two-dimensional images will not be reduced. Thus any movement during the examination will affect the images—but both images will be distorted similarly (which is important for the dual-energy evaluation).

If the scanning is performed with a stepwise scanning movement, preferably but not necessarily, two recordings are made at each step of the scanning. However, the filter device has only to alter its operation mode once at each step, i.e. at every second line image recording, since the recordings at every second step may start with the filter in one operation mode and the recordings at the other remaining steps may start with the filter in the other operation mode.

For this solution, the misalignment in the pixel-to-pixel comparison will not generally be present at all, whereas the two-line detection time will be as indicated above.

The dual-energy detector apparatus can be used to measure the bone mineral density of humans. Normally the bone is surrounded by an unknown amount of tissue. One commonly used method to estimate the amount of bone is to detect transmitted X-rays at two different X-ray energies. One image is recorded at X-ray energies where bone and tissue absorb X-rays very differently, typically at about 40 keV where the differential absorption coefficient has a maximum. Another image is recorded at energies where bone and tissue absorb X-rays in a similar way, typically at energies above 70 keV. From these two measurements the amount of bone is estimated. Since the two separate images are recorded simultaneously, i.e. each pair of line images at the two different energies are recorded close in time, problems due to movements of the object between the two exposures are heavily reduced. This is often achieved by making two separate exposures using two different acceleration voltages of the X-ray tube and different filters in the beam path.

With the current invention the dual-energy measurements are made simultaneously (or nearly simultaneously) using a single acceleration voltage of a single X-ray tube (normally 70 kV or higher) and a specifically designed filter to produce a low energy spectrum and a high energy spectrum, respectively, simultaneously (or nearly simultaneously).

It shall further be appreciated that while the detector unit in the description above has been described as a gaseous-based ionization detector, wherein the freed electrons are drifted in a direction essentially perpendicular to the direction of the incident radiation, the present invention is not limited to such a detector. In fact, virtually any kind of detector can be used in any of the preferred embodiments of the present invention as long as it is a detector capable of recording one-dimensional images of ionizing radiation, to which it is exposed. Examples of such detectors are scintillator-based detectors, PIN-diode arrays, TFT (thin film transistor) arrays, CCD (charged coupled device) arrays, CMOS circuits, or any other type of semiconductor devices.

Figure 3:
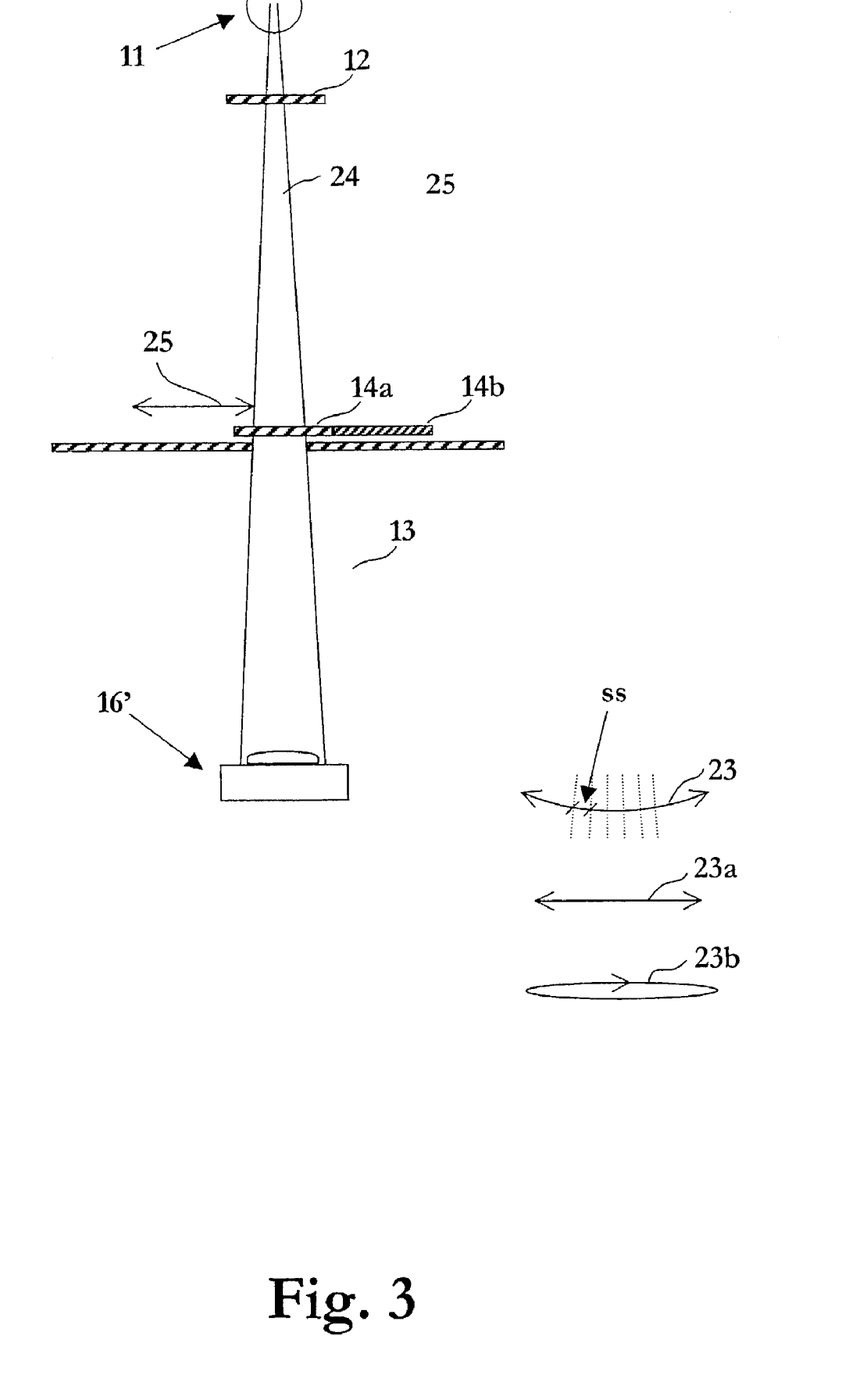
FIG. 3 is a schematic enlarged cross-sectional view of main components of an apparatus for dual-energy scanning-based X-ray imaging according to still a preferred embodiment of the invention.

FIG. 3 is a schematic enlarged cross-sectional view similar to the FIG. 2 cross-sectional view, but which illustrates portions of a detector apparatus based on a linear semiconductor array 16', which may be used in the dual-energy scanning-based detector apparatus of the present invention.

Figure 4:
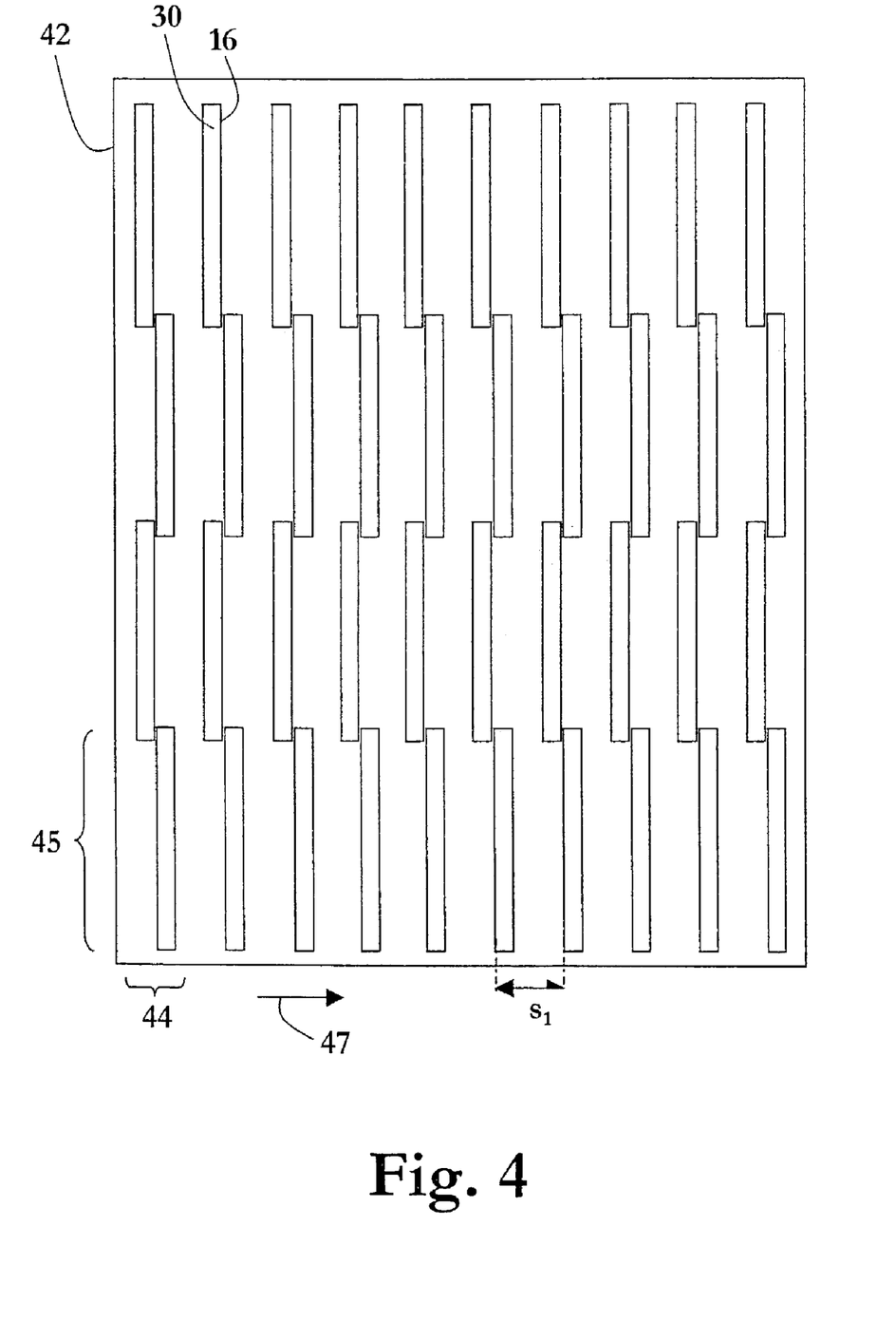
FIG. 4 is a schematic top plan view of a detector arrangement to be used in an apparatus for dual-energy scanning-based X-ray imaging according to yet a preferred embodiment.
Figure 5:
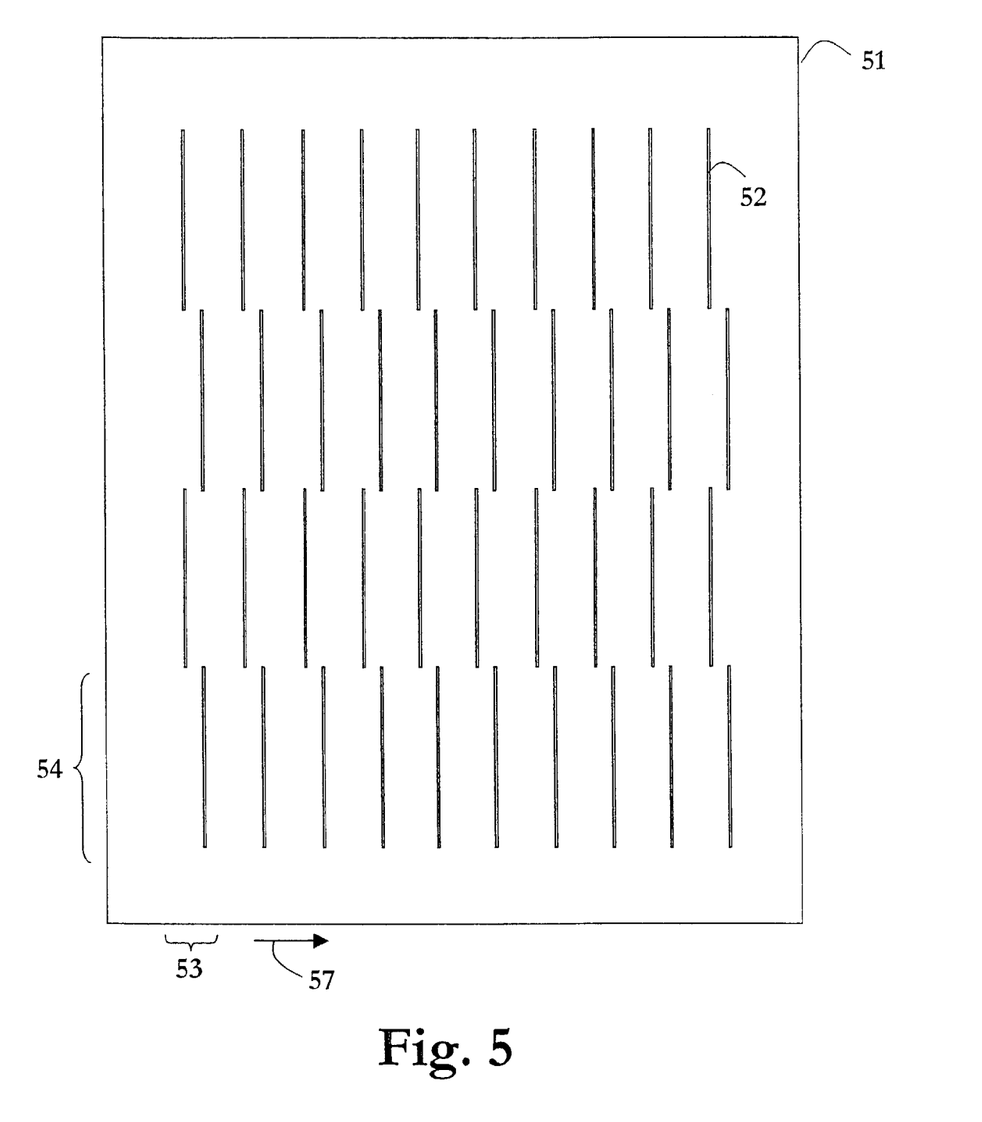
FIG. 5 is a schematic top plan view of a collimator arrangement to be used with the detector arrangement of FIG. 4.
Figure 6:
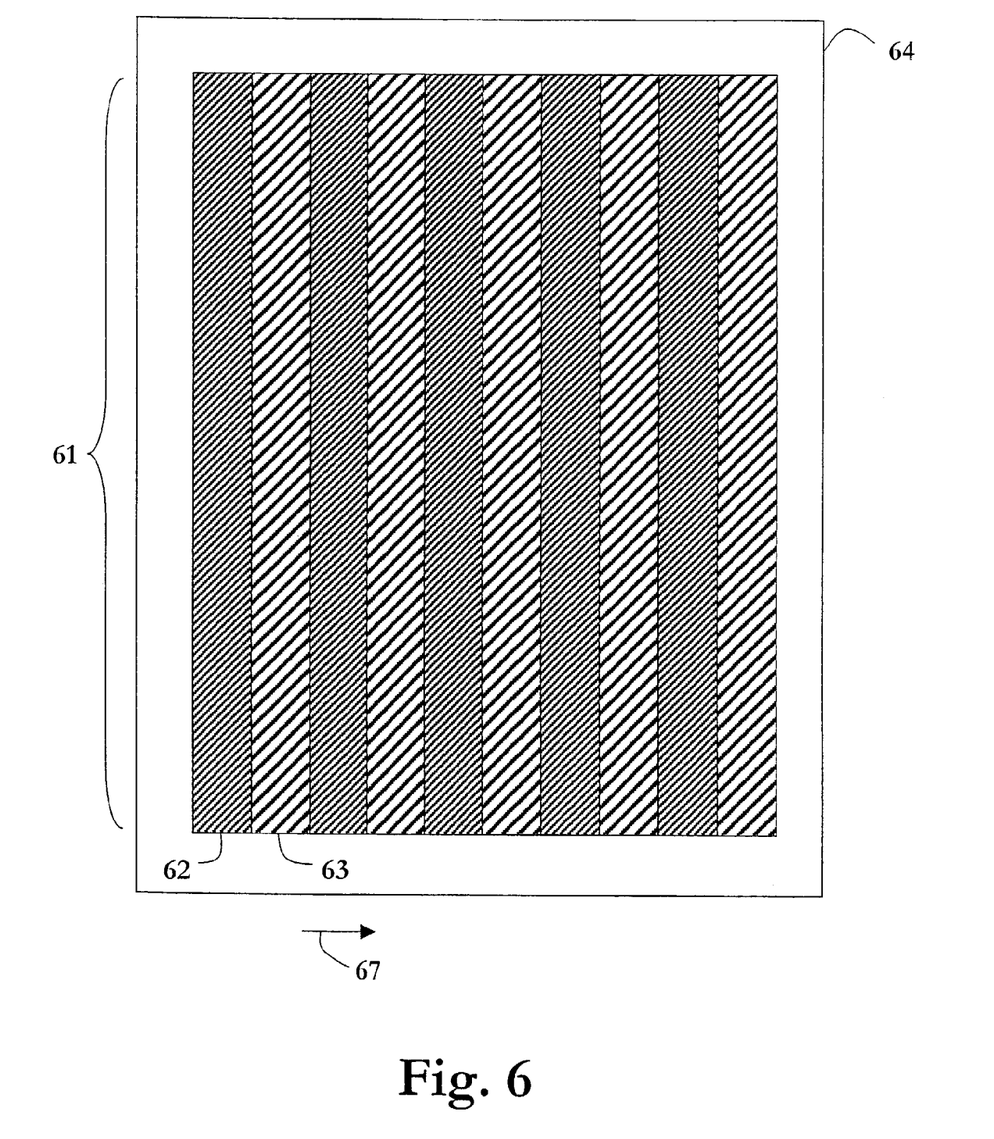
FIG. 6 is a schematic top plan view of a filter arrangement to be used with the detector arrangement of FIG. 4.

With reference next to FIGS. 4–6, which are schematic top plan views of a detector arrangement, a collimator arrangement, and a filter arrangement, respectively to be used in an apparatus for dual-energy scanning-based X-ray imaging yet a preferred embodiment of the present invention will be described.

The apparatus for dual-energy scanning-based X-ray imaging may be similar to the FIG. 1 apparatus, but where the filter device 14, the collimator 13, and the detector unit 16 are exchanged for the arrangements of FIGS. 4–6.

The detector arrangement includes a plurality of line detector units 16 arranged on a common support structure 42 in a two-dimensional array with their respective entrance windows 30 facing upwards. For illustrative purposes FIG. 4 only includes a matrix of 4×10 detector units, i.e. each row 44 includes four detector units and each stack 45 includes ten detector units 16, even though it shall be appreciated that the arrangement may include many more units. For instance if the detector units in each stack 45 are spaced apart by $s_1=4$ mm and an area of typically 20×20 cm² shall be covered, each stack may include 50 detector units. The width of each line detector unit may for instance be 40–60 mm.

It shall be noted that the detector units 16 in each row 44 are preferably arranged in a staggered manner. If the detector units 16 are not capable of detecting at their extreme side portions e.g. due to the presence of sidewalls or spacers, the staggering of the units provides for complete coverage and any "dead" zones are avoided. Where the entrance slit of one detector unit ends in each row 44, the entrance slit of a further detector unit begins. Nevertheless, the present invention is fully applicable to detector arrangements having detector units in other stacked configurations.

It shall be appreciated that instead of arranging multiple individual detector units 16 with separate gas-tight confinements in the detector arrangement, a detector arrangement having a common gas-tight enclosing for all individual detector units may be provided (not illustrated). Such a detector box would include the support 42, sidewalls, and a front cover including the entrance windows 30.

The collimator arrangement, which is optional, is of a radiation-absorbing material 51, e.g. tungsten, and includes a plurality of radiation transparent slits 52 arranged in rows 53 and stacks 54. The radiation transparent slits 52 are aligned with the entrance slits of the detector units of the FIG. 4 arrangement, so that each planar radiation beam as produced by the collimator 51 when being arranged in the path of a radiation beam is transmitted through a respective portion of the object to be examined and is entered into a respective one of the detector units 16 in the FIG. 4 detector arrangement. The collimator 51 is then moved together with the detector arrangement during scanning across the object in a pivoting or translative movement essentially in the direction of arrows 47 (FIG. 4) and 57 (FIG. 5) to keep the alignment.

The inventive filter arrangement comprises an array 61 of filter sections 62, 63 carried by a frame support 64. The filter sections are of two different kinds, where every second filter section 62 in the array has a first filter characteristic and the other filter sections 63 in the array have each a second filter characteristic. The filter arrangement is aligned with the collimator arrangement so that each of the planar radiation beams will have been filtered by a respective one of the filter sections when impinging on the object. Note that the filter arrangement of FIG. 6 does not need a particular moving mechanism (as the filter device of FIG. 1), but is moved only in accordance with the scanning movement as indicated by arrow 67.

The alignment between the radiation source (point source, line source or 2D source), the filter arrangement, the collimator arrangement, and the detector arrangement provides for collimated and row-selectively filtered multiple planar radiation beams entering the individual detector units 16 of the detector arrangement. Thus provided divergent radiation the detector units are arranged to point towards the radiation source used such that radiation from the radiation source can enter the respective detector unit. For the same reason the collimator 51 has slits that are less spaced apart than the detector units and narrower that the detector unit entrance slits, and the width of the filter sections of the filter arrangement is smaller than the width of the rows of the detector arrangement to obtain a proper alignment.

Scanning is performed at least a distance corresponding to two times the distance between two adjacent line detector units 16 in each stack to record a sufficient number of line images to obtain a complete two-dimensional image for each one of the two kinds of filtration (as typically one two-dimensional image is obtained when scanning a distance corresponding to the distance between two adjacent line detectors in a stack.

For such a solution, the misalignment in the pixel-to-pixel comparison will not generally be present at all, whereas the two-line detection time will correspond to the time of scanning a distance corresponding to the inter-detector unit distance $s_1$, which for this purpose should be very short. The total scanning time is reduced by a factor corresponding to half the number of the detector units in each stack.

Note that in the embodiment described above, a detector array comprising a single stack of detector units may be employed instead of the FIG. 4 arrangement. Obviously, the collimator arrangement, and optionally the filter arrangement, has to be modified in such an instance.

Figure 7:
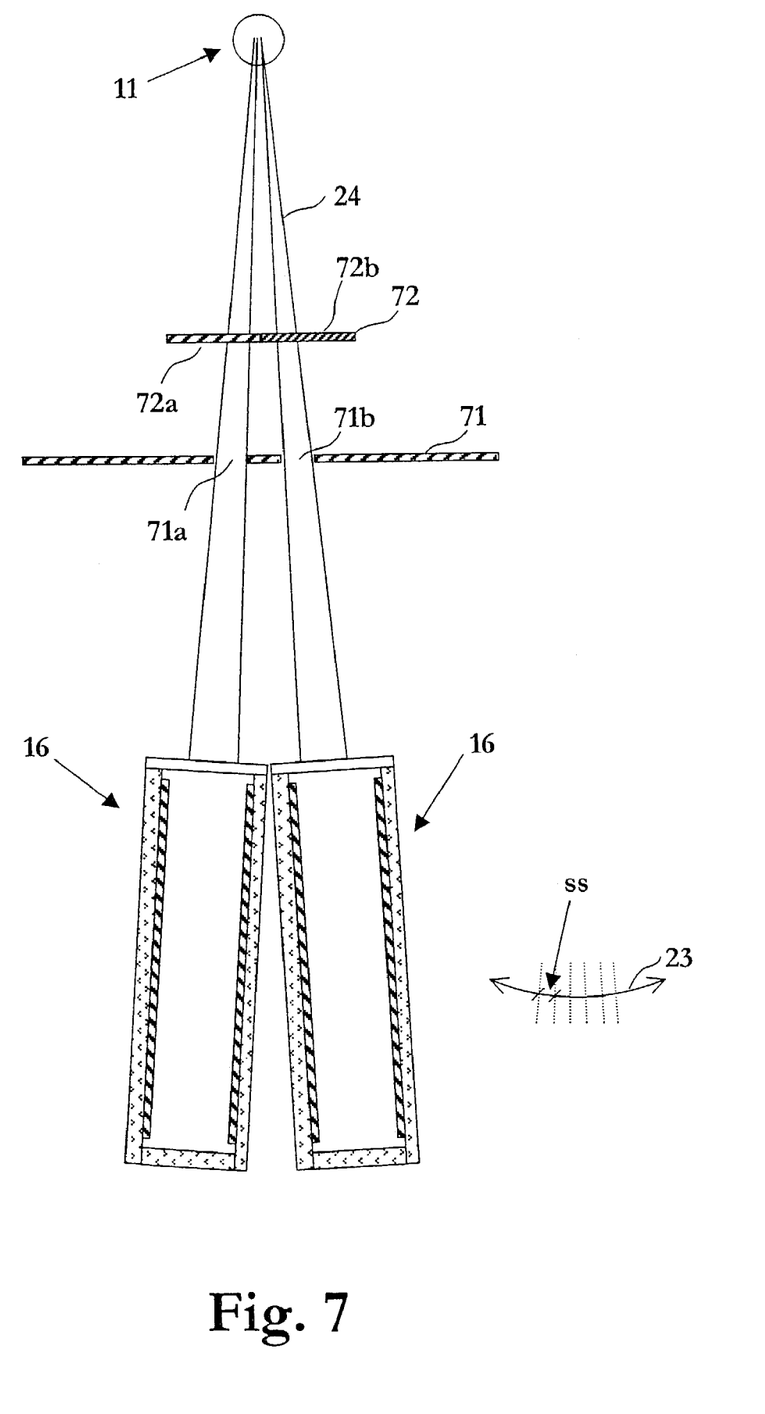
FIG. 7 is a schematic enlarged cross-sectional view of main components of an apparatus for dual-energy scanning-based X-ray imaging according to still a preferred embodiment of the invention.

It shall be appreciated that a further alternative is to employ a detector arrangement comprising only two detector units 16 very closely together in a short detector stack as illustrated in FIG. 7. The collimator arrangement 71 and filter arrangement 72 are modified accordingly to only comprise two collimator slits 71a–b and two filter sections 72a–b, respectively. Scanning has now to be performed a distance equal to the object size in the direction of scanning. However, the distance between the detector units may be made very short without having to bring together a very large number of detector units. Here, the two-line detection time may be very short to the expense of a prolonged total detection time.

It shall further be appreciated that ideas from the FIGS. 1–2 embodiment (or the FIG. 3 embodiment) and the FIGS. 4–6 embodiment may be brought together to form yet two other preferred embodiments of the present invention.

Figure 8:
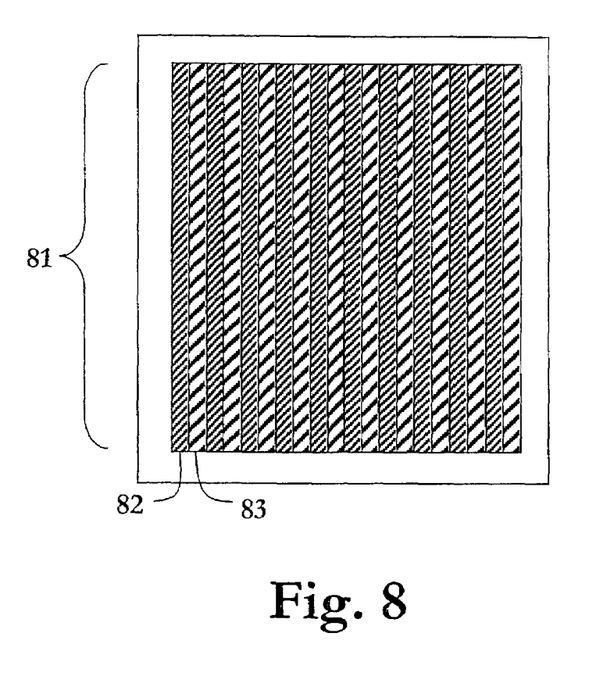
FIG. 8 is a schematic top plan view of a filter arrangement to be used in an apparatus for dual-energy scanning-based X-ray imaging according to yet a preferred embodiment.

In the first of these embodiments the detector arrangement and collimator arrangement of FIGS. 4–5 are used together with a filter arrangement as illustrated in FIG. 8. The filter arrangement of FIG. 8 has ten rows 81 (corresponding to the number of rows in the detector arrangement), each including two filter sections 82, 83 having different filter characteristics. The filter arrangement is provided with a particular moving mechanism (similar to the one described with reference to FIGS. 1–2) and connected to the scanning movement so that, during scanning, each of the ionizing radiation beams will have been filtered by a respective filter row, alternately using the two filter sections thereof, when impinging on the object. The scanning, which may be continuous or stepwise, is performed at least a distance corresponding to the distance between two adjacent detector units in the stacks.

The misalignment, i.e. the pixel-to-pixel correspondence, in the dual-energy image evaluation and the time needed to record two adjacent dual-energy line images are similar to the FIGS. 1–2 embodiment, but the total scanning time will be reduced by a factor corresponding to the number of detector units in each stack.

Figure 9:
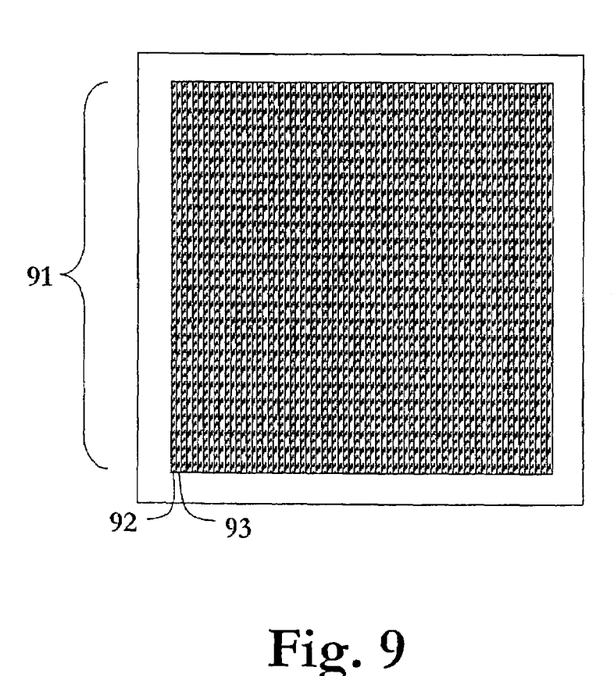
FIG. 9 is a schematic top plan view of a filter arrangement to be used in an apparatus for dual-energy scanning-based X-ray imaging according to still a preferred embodiment.

In the second of these embodiments the filter device 14 in the apparatus of FIGS. 1–2 is exchanged for a filter arrangement as illustrated in FIG. 9. This filter arrangement comprises an array 91 with a large number of filter sections of two alternating kinds 92, 93 having different filter characteristics. The filter arrangement is intended to be fixedly mounted to the vertical stand 18, i.e. kept still during scanning. The distance between adjacent filter sections is preferably adapted to the scanning step ss so that every second line image recording is performed with radiation filtered by one kind of filter section, and the other line image recordings are performed with radiation filtered by the other kind of filter section (only one recording is performed at each scanning step independent of whether the scanning is continuous or stepwise).

This embodiment is very similar to the continuous scanning technique using the FIGS. 1–2 embodiment, but instead of moving the filter device "on top" of the scanning movement, the filter is held completely still during the scan (and is provided with a structure adapted to the scanning step used).

What is claimed is:

1. A dual-energy scanning-based radiation detecting apparatus comprising:
   a line detector;
   a device for scanning said line detector across an object to be examined while said line detector is exposed to an ionizing radiation beam, which has impinged on said object, to thereby record a plurality of line images of said object;
   a filter device arranged in the path of said ionizing radiation beam upstream of said object to filtrate said ionizing radiation beam, the filter device being capable of operating in two operation modes having different filter characteristics; and
   a control device for altering operation mode of the filter device subsequent to at least every second of said line images being recorded, wherein
   said device for scanning said line detector across said object is adapted to scan said line detector in stepwise movements and said line detector is adapted to be exposed and read out when being still between each of said stepwise movements to thereby record said plurality of line images of said object; and
   said control device is adapted to alter the operation mode of said filter device once while said line detector is still between each of said stepwise movements at each to each one of said line images being recorded and said line detector is adapted, when being still between each of said stepwise movements, to be exposed and read out once before and once after said operation mode alteration performed while said line detector is still.

2. The apparatus of claim 1 wherein said filter device comprises at least two filter sections which sections are capable of being arranged, one at a time, in the path of said radiation beam to form said two operation modes.

3. The apparatus of claim 2 wherein said control device comprises a moving mechanism for inserting said at least two filter sections, one at a time, in the path of said radiation beam.

4. The apparatus of claim 1 wherein said line detector is a gaseous-based ionization detector, wherein electrons freed as a result of ionization by said ionizing radiation beam are accelerated in a direction essentially perpendicular to the direction of said ionizing radiation beam.

5. The apparatus of claim 1 wherein said line detector is any of a scintillator-based detector, a PIN-diode array, a TFT array, a CCD array, a liquid-based detector, and a solid-state detector.

6. The apparatus of claim 1 comprising an X-ray tube for producing said ionizing radiation beam, said X-ray tube having an operating voltage, which is kept essentially constant during the scanning of said line detector across the object to be examined.

7. A dual-energy scanning-based radiation detecting apparatus comprising:
   a plurality of stacked line detectors;
   a device provided for scanning said plurality of stacked line detectors across an object to be examined substantially in a linear path parallel with the stack of line detectors while each of said plurality of stacked line detectors is exposed to an ionizing radiation beam, which has been transmitted through said object, to thereby record a plurality of line images of radiation as transmitted through said object;
   a filter device arranged in the path of said ionizing radiation beams upstream of said object to filtrate said ionizing radiation beams, the filter device comprising an array of filter sections aligned with said ionizing radiation beams during scanning so that each of said ionizing radiation beams will have been filtered by a respective one of said filter sections when impinging on said object, where every second filter section in the array has a first filter characteristic and the other filter sections in the array have each a second filter characteristic; and
   said device for scanning said plurality of stacked line detector scans a distance corresponding to two times the distance between two adjacent line detectors of said plurality of stacked line detectors to create two two-dimensional images of radiation as transmitted through said object, one two-dimensional image of radiation which has been filtered by a filter section having the first filter characteristic, and one two-dimensional image of radiation which has been filtered by a filter section having the second filter characteristic, wherein the number of said plurality of stacked line detectors is at least 10;

said at least 10 stacked line detectors are essentially evenly distributed over the entire two-dimensional images; and said device for scanning said plurality of stacked line detectors scans a maximum distance corresponding to the width of the two-dimensional images divided by five to create said two-dimensional images of radiation.

8. The apparatus of claim 7 comprising an X-ray tube for producing said ionizing radiation beam, said X-ray tube having an operating voltage, which is kept essentially constant during the scanning of said plurality of stacked line detectors across the object to be examined.

9. The apparatus of claim 7 wherein each one of said plurality of stacked line detectors comprises multiple line detector units arranged in parallel.

10. The apparatus of claim 9 wherein said multiple line detector units are at least 4.

11. The apparatus of claim 10 wherein each one of said multiple line detector units is 40–60 mm wide.

12. The apparatus of claim 10 wherein said multiple line detector units are arranged in a staggered manner.

13. A dual-energy scanning-based radiation detecting method comprising the steps of:

scanning a plurality of stacked line detectors across an object to be examined substantially in a linear path parallel with the stack of line detectors while each of said plurality of stacked line detectors is exposed to an ionizing radiation beam, which has been transmitted through said object, to thereby record a plurality of line images of radiation as transmitted through said object;

arranging a filter device in the path of said ionizing radiation beams upstream of said object to filtrate said ionizing radiation beams, the filter device comprising an array of filter sections; and having said filter sections aligned with said ionizing radiation beams during scanning so that each of said ionizing radiation beams will have been filtered by a respective one of said filter sections when impinging on said object, where every second filter section in the array has a first filter characteristic and the other filter sections in the array have each a second filter characteristic; wherein said scanning said plurality of stacked line detector is performed a distance corresponding to two times the distance between two adjacent line detectors of said plurality of stacked line detectors to create two two-dimensional images of radiation as transmitted through said object, one two-dimensional image of radiation which has been filtered by a filter section having the first filter characteristic, and one two-dimensional image of radiation which has been filtered by a filter section having the second filter characteristic, wherein the number of said plurality of stacked line detectors is at least 10;

said at least 10 stacked line detectors are essentially evenly distributed over the entire two-dimensional images; and said scanning said plurality of stacked line detectors scans a maximum distance corresponding to the width of the two-dimensional images divided by five to create said two-dimensional images of radiation.

14. A dual-energy scanning-based radiation detecting apparatus comprising:

a plurality of stacked line detectors;

a device provided for scanning said plurality of stacked line detectors across an object to be examined while each of said plurality of stacked line detectors is exposed to an ionizing radiation beam, which has been transmitted through said object, to thereby record a plurality of line images of radiation as transmitted through said object;

a filter device comprising filter sections of two kinds having different filter characteristics alternately arranged in an array, wherein the number of filter sections of each of the two kinds is higher than the number of said plurality of stacked line detectors;

the filter device is held still during scanning so that the filter sections of each of the two kinds are alternately arranged in the radiation paths of said ionizing radiation beams upstream of said object to filtrate said ionizing radiation beams; and said device for scanning said plurality of stacked line detector scans a distance corresponding to the distance between two adjacent line detectors of said plurality of stacked line detectors to create two two-dimensional images of radiation as transmitted through said object, one two-dimensional image of radiation which has been filtered by a filter section having a first filter characteristic, and one two-dimensional image of radiation which has been filtered by a filter section having a second filter characteristic different from the first filter characteristic, wherein the number of the filter sections of the two kinds are adapted to the scanning step of said scanning so that each of said plurality of line detectors record line images of radiation, which has alternately passed through a filter section having the first filter characteristic and a filter section having the second filter characteristic.

* * * * *